(12) United States Patent
Sankar et al.

(10) Patent No.: US 12,223,669 B2
(45) Date of Patent: Feb. 11, 2025

(54) TOUCHLESS WRIST MEASUREMENT

(71) Applicant: Apple Inc., Cupertino, CA (US)

(72) Inventors: Aditya Sankar, Seattle, WA (US); Qi Shan, Mercer Island, WA (US); Shreyas V. Joshi, Seattle, WA (US); David Guera Cobo, Seattle, WA (US); Fareeha Irfan, Seattle, WA (US); Bryan M. Perfetti, San Jose, CA (US)

(73) Assignee: Apple Inc., Cupertino, CA (US)

( * ) Notice: Subject to any disclaimer, the term of this patent is extended or adjusted under 35 U.S.C. 154(b) by 514 days.

(21) Appl. No.: 17/670,686

(22) Filed: Feb. 14, 2022

(65) Prior Publication Data
US 2022/0262025 A1   Aug. 18, 2022

Related U.S. Application Data

(60) Provisional application No. 63/150,621, filed on Feb. 18, 2021.

(51) Int. Cl.
*G06T 7/55* (2017.01)
*G01B 11/08* (2006.01)
(Continued)

(52) U.S. Cl.
CPC ............. *G06T 7/55* (2017.01); *G01B 11/08* (2013.01); *G06N 3/04* (2013.01); *G06N 20/00* (2019.01); *G06T 2207/10028* (2013.01)

(58) Field of Classification Search
CPC .... G06T 7/50; G06T 7/55; G06T 7/62; G06T 2207/10016; G06T 2207/10028;
(Continued)

(56) References Cited

U.S. PATENT DOCUMENTS 9,460,342 B1 * 10/2016 Freund ............... G06Q 30/0621
10,002,377 B1 * 6/2018 Johnson ............. G06Q 30/0631
(Continued)

FOREIGN PATENT DOCUMENTS

JP       2020-177462 A    10/2020
KR  10-2016-0070744 A     6/2016
(Continued)

OTHER PUBLICATIONS

Korean Intellectual Property Office, Notice of Preliminary Rejection issued Jan. 2, 2024 which pertains to Korean Patent Application No. 10-2022-0020835, English Translation, 11 pages.
(Continued)

*Primary Examiner* — Ping Y Hsieh
*Assistant Examiner* — Jose M Torres
(74) *Attorney, Agent, or Firm* — Thompson Hine LLP

(57) ABSTRACT

Various implementations disclosed herein include devices, systems, and methods that determine a wrist measurement or watch band size using depth data captured by a depth sensor from one or more rotational orientations of the wrist. In some implementations, depth data captured by a depth sensor including at least two depth map images of a wrist from different angles is obtained. In some implementations, an output is generated based on inputting the depth data into a machine learning model, the output corresponding to circumference of the wrist or a watch band size of the wrist. Then, a watch band size recommendation is provided based on the output.

20 Claims, 10 Drawing Sheets

(51) Int. Cl.
*G06N 3/04* (2023.01)
*G06N 20/00* (2019.01)

(58) Field of Classification Search
CPC .......... G06T 2207/20084; G01B 11/02; G01B 11/022; G01B 11/026; G01B 11/08; G01B 11/24; G01B 11/2518; G06N 3/04; G06N 3/045; G06N 3/08; G06N 20/00; A61B 5/0033; A61B 5/0059; A61B 5/107; A61B 5/1075; A61B 5/1079; A44C 5/00

See application file for complete search history.

(56) References Cited

U.S. PATENT DOCUMENTS

| | | | |
|---|---|---|---|
| 10,701,999 B1* | 7/2020 | Borenstein | G06Q 30/0623 |
| 11,232,629 B1* | 1/2022 | Seymore | H04N 23/64 |
| 11,721,035 B2* | 8/2023 | Do | G06F 1/1626 |
| | | | 345/633 |
| 2014/0300907 A1* | 10/2014 | Kimmel | G06T 7/62 |
| | | | 356/625 |
| 2015/0302597 A1* | 10/2015 | Bentson | G06V 40/103 |
| | | | 382/154 |
| 2016/0162673 A1* | 6/2016 | Kutliroff | G06F 18/28 |
| | | | 382/115 |
| 2019/0310716 A1* | 10/2019 | Sinha | G06V 10/454 |
| 2020/0013182 A1* | 1/2020 | Sompura | G06T 7/62 |
| 2020/0319015 A1* | 10/2020 | Kamiyama | A61B 5/1079 |
| 2021/0049811 A1* | 2/2021 | Fedyukov | G06T 7/60 |
| 2021/0082179 A1* | 3/2021 | Fedyukov | G06T 7/60 |
| 2021/0118038 A1* | 4/2021 | Schmidt | G06T 11/00 |
| 2022/0007798 A1* | 1/2022 | Grozel | G06V 40/107 |
| 2022/0258049 A1* | 8/2022 | Kanani | G06Q 30/0621 |
| 2023/0047211 A1* | 2/2023 | Abuelwafa | G06T 7/344 |
| 2023/0293045 A1* | 9/2023 | Cheng | A61B 5/1079 |
| | | | 600/587 |
| 2024/0148321 A1* | 5/2024 | Chhatkuli | G16H 10/60 |
| 2024/0185512 A1* | 6/2024 | Furko | G06V 40/107 |

FOREIGN PATENT DOCUMENTS

| | | |
|---|---|---|
| KR | 10-2108931 B1 | 5/2020 |
| KR | 10-2149395 B1 | 8/2020 |

OTHER PUBLICATIONS

Sunyoto, A. et al.; "Wrist Detection on a Minimum Bounding Box and Geometric Figures"; Journal of King Saud University—Computer and Information Sciences, May (2018); pp. 1-9, https://doi.org/10.1016/j.jkuci.201805.005.

* cited by examiner

TOUCHLESS WRIST MEASUREMENT

CROSS-REFERENCE TO RELATED APPLICATIONS

This Application claims the benefit of U.S. Provisional Application Ser. No. 63/150,621 filed Feb. 18, 2021, which is incorporated herein in its entirety.

TECHNICAL FIELD

The present disclosure generally relates to electronic devices that perform touchless wrist measurement and, in particular, to systems, methods, and devices that determine a wrist measurement or watch band size using depth data captured by a depth sensor of an electronic device.

BACKGROUND

Existing measuring techniques have various disadvantages with respect to measuring a person's wrist. Such techniques may require special measuring equipment such as a body measuring ruler or tape that require contact with the person's wrist and that may be cumbersome to use and subject to error.

SUMMARY

Various implementations disclosed herein include devices, systems, and methods that determine a wrist measurement or watch band size using depth data captured by a depth sensor. In some implementations, wrist measurement techniques are touchless. In some implementations, the wrist measurement techniques are performed by a trained technician in a brick and mortar retail store. Alternatively, the wrist measurement techniques are performed by an individual using an electronic device like a smartphone that includes the depth sensor. For example, the electronic device is placed on a surface with the depth sensor facing up, and a user may rotate their hand/wrist above the electronic device while at least two depth map images of the wrist are captured during a wrist scanning process. In some implementations, the depth data includes at least two depth map images of a wrist from different angles sufficiently separated to accurately represent the wrist's circumference. For example, one of the depth map images of the user's wrist may be captured with the palm facing the depth sensor and the other of the depth map images of the user's wrist is captured with the palm facing to the side (e.g., approximately 90° rotation). In some implementations, the depth data is input into a machine learning (ML) model that outputs a measurement corresponding to circumference of the wrist and/or a watch band size among a plurality of band sizes. In some implementations, the ML model is a convolutional neural network (CNN) regressor.

In some implementations, at an electronic device having a processor, a method includes obtaining depth data captured by a depth sensor, the depth data including at least two depth map images of a wrist from different angles. In some implementations, an output is generated based on inputting the depth data into a machine learning model, the output corresponding to circumference of the wrist or a watch band size of the wrist, and a watch band size recommendation is provided based on the output.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

Figure 1:
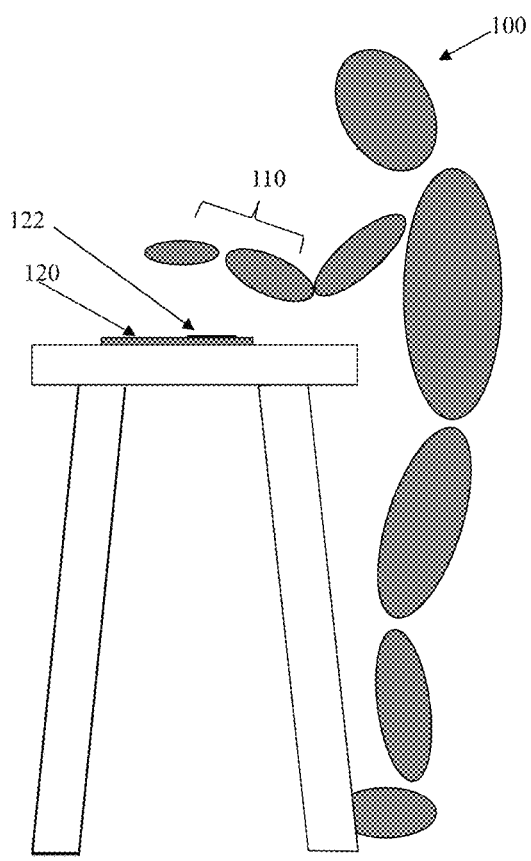
FIGS. 1-5 illustrate an example wrist measurement technique in accordance with some implementations.

In accordance with common practice, the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects or variants do not include all of the specific details described herein. Moreover, well-known systems, methods, components, devices and circuits have not been described in exhaustive detail so as not to obscure more pertinent aspects of the example implementations described herein.

Various implementations disclosed herein include devices, systems, and methods that determine a wrist measurement and/or watch band size using depth data captured by a depth sensor. In some implementations, wrist measurement techniques are touchless. In some implementations, the wrist measurement techniques are performed by an individual using an electronic device like a smartphone that includes a depth sensor. The electronic device may be placed on a surface with the depth sensor facing up, and a user may rotate their hand/wrist above the electronic device while at least two depth map images of the wrist are captured during a wrist scanning process. In some implementations, one of the depth map images of the user's wrist is captured with the palm facing the depth sensor and the other of the depth map images of the user's wrist is captured with the palm facing to the side. In some implementations, the depth data is input into a machine learning (ML) model that outputs a measurement corresponding to a circumference of the wrist and/or a watch band size among a plurality of band sizes. Optionally, the depth map images may include depth values for portions of a hand, all of the hand, and/or portions of the arm above the wrist. In some implementations, guidance regarding positioning of the wrist is provided while the depth data is obtained by the depth sensor.

In some implementations, watch bands come in a plurality of sizes. Further, a first watch type (e.g., wide) may come in a first plurality of fixed sizes and a second watch type (e.g., narrow) may come in a second plurality of fixed sizes based on wrist circumference. However, watch band sizes may overlap between a first watch type and a second watch type. In some implementations, the watch band is not adjustable (e.g., no clasp, buckle, notch, etc.), although a non-adjustable watch band may stretch a little to slide over the hand and onto the wrist. An accurate wrist measurement is especially useful for non-adjustable watches.

FIGS. 1-5 illustrate an example wrist measurement technique in accordance with some implementations. As shown in FIG. 1, the wrist measurement technique may be implemented in an electronic device 120. In FIG. 1, the electronic device 120 includes a depth sensor 122 that faces a wrist 110 of a user 100. In some implementations, two depth images of the wrist 110 captured by the depth sensor 122 are used to determine a wrist measurement and/or watch band size.

In some implementations, a set of more than two depth map images are obtained and the two depth map images are selected from the set based on determining that the two depth map images correspond to at least a threshold difference in viewpoint (e.g., 50°, 60°, 70°, 80°, 90°) that is sufficient to provide a sufficient level of accuracy for an intended use case. In one example, a threshold difference in viewpoint is selected based on determining that difference is sufficient to identify two different ellipse parameters representing the wrist's shape and size from which a wrist circumference can be determined. Identifying the ellipse parameters may require a threshold difference in viewpoint. Optionally, the depth map images may include depth values for portions of a hand, all of the hand, and/or other portions of the arm, e.g., the arm up to the elbow. In some implementations, guidance regarding positioning of the wrist or depth sensor is provided while the depth data is obtained.

Figure 2:
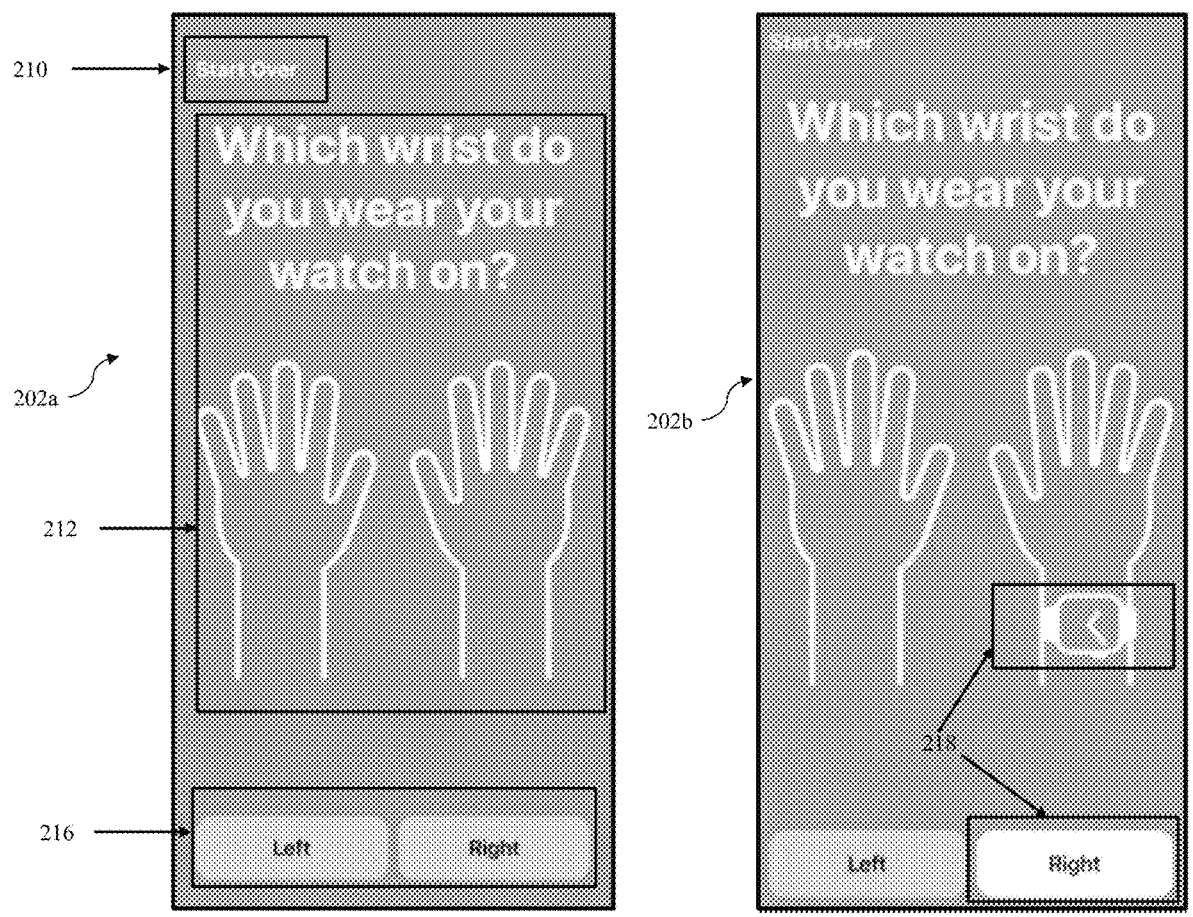

Upon initiating the wrist measurement technique in the electronic device 120, an initialization screen 202 may be provided at the electronic device 120. As shown in FIG. 2, a first image 202a of the initialization screen 202 includes a wrist selection indicator 212 and a wrist selection actuator 216. In some implementations, when the user 100 selects the right wrist to be measured at the wrist selection actuator 216, the right wrist selection is indicated in wrist selection image 202b using a wrist selection confirmation 218 in a second image 202b of the initialization screen 202. In some implementations, a start over selection 210 is continuously available during the entire wrist measurement technique.

Figure 3:
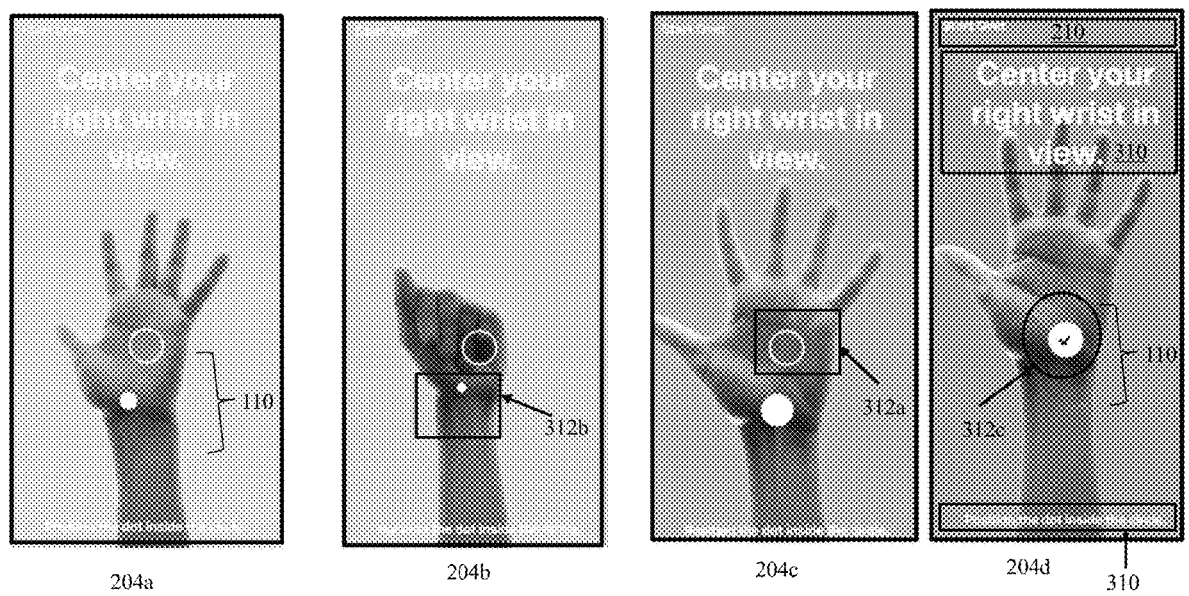

Upon selection on a wrist to be measured, a first wrist measurement screen 204 may be provided at the electronic device 120. As shown in FIG. 3, first wrist measurement screen 204 includes an instruction area 310, a fixed indicator 312a, a variable indicator 312b, and a first wrist measurement complete indicator 312c. For example, the instruction area 310 may say "center your right wrist palm down in the view below" and "position the solid dot inside to fill the hollow circle" (e.g., move the variable indicator 312b relative to the fixed indicator 312a). In some implementations, the fixed indicator 312a represents a preset height above the depth sensor 122. Further, the variable indicator 312b moves with the wrist 110 and increases in size as the variable indicator 312b approaches the depth sensor 122. In some implementations, the first wrist measurement screen 204 includes a view of the area above the depth sensor 122 (e.g., the area in which a first depth measurement of the right wrist 110 is being taken). As shown in FIG. 3, a series of example images 204a, 204b, 204c of the first measurement screen 204 include the wrist 110, the fixed indicator 312a, and the variable indicator 312b until the first wrist measurement complete indicator 312c is displayed in example image 204d.

Figure 4:
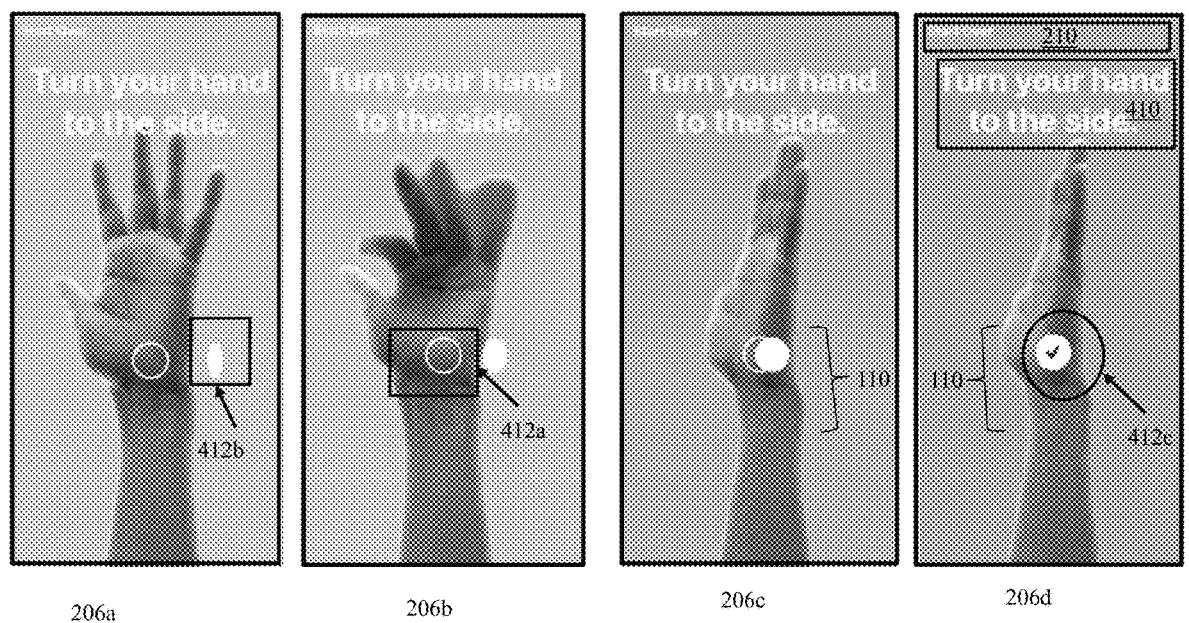

Upon completion of a first wrist measurement, a second wrist measurement screen 206 may be provided at the electronic device. As shown in FIG. 4, the second wrist measurement screen 206 includes an instruction area 410, a fixed indicator 412a, a variable indicator 412b, and a second wrist measurement complete indicator 412c. For example, the instruction area 410 may say "turn your hand to the side and center your wrist in the view below" and "position the dot inside to fill the circle" (e.g., move the variable indicator 412b to fill to the fixed indicator 412a). In some implementations, the fixed indicator 412a represents a preset height above the depth sensor 122, and the variable indicator 412b moves with the wrist 110 to indicate the distance from the wrist 110 to the depth sensor 122. For example, the variable indicator 412b may increase in size as the variable indicator 412b approaches the depth sensor 122. In some implementations, the second wrist measurement screen 206 includes a view of the area above the depth sensor 122 (e.g., the area in which a second depth measurement of the right wrist 110 is being taken). As shown in FIG. 4, a series of example images 206a, 206b, 206c of the second measurement screen 206 include the wrist 110, the fixed indicator 412a, and the variable indicator 412b until the second wrist measurement complete indicator 412c is displayed in example image 206d.

Figure 5:
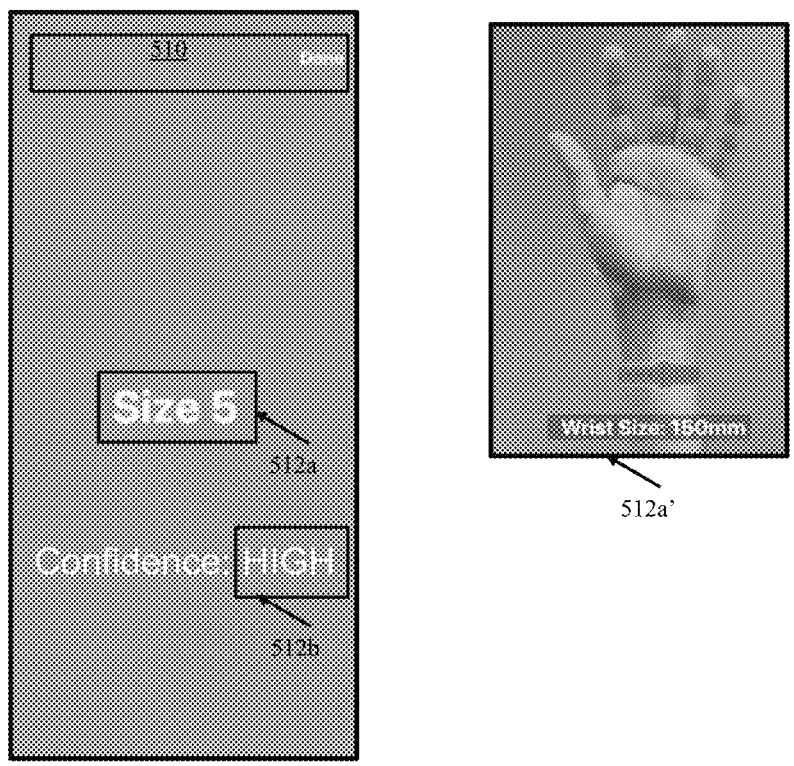

In some implementations, two (or more) depth measurements or images of the wrist 110 captured by the depth sensor 122 are used to determine a wrist measurement or watch band size. In some implementations, a measurement output screen 208 includes a measurement indicator. As shown in FIG. 5, the measurement indicator 512a provides a watch band size being "size 5". In some implementations, the measurement output screen 508 includes a measurement complete indicator 510 and a measurement confidence indicator 512b. As shown in FIG. 5, the measurement indicator 512a provides a watch band size being "size 5" with a "high" measurement confidence indicator 512b.

In some alternate implementations, the wrist circumference is the output of the wrist measurement technique. As shown in FIG. 5, the measurement indicator 512a' provides the wrist circumference that may be graphically displayed on a view of the wrist 110 of the user 100. In other implementations, the band size or wrist circumference may be displayed as a 3D virtual object (e.g., with the watch and/or wrist).

In some implementations, the measurement confidence indicator 512b outputs a relative value for the measurement confidence indicator 512b (e.g., high, good, average, poor) or only outputs an indicator when the confidence is such that an output of the wrist measurement technique is a recommendation to re-do the wrist measurement for the user 100. In some implementations, the measurement confidence indicator 512b outputs a numerical value between zero and 100.

In some implementations, the two depth images of the wrist are input into a machine learning (ML) model (e.g., a neural network) that is trained to output wrist measurements or 1 size (e.g., 2 sizes for example when the confidence is low or the circumference measurement is equal/close between two sizes) from among a plurality of watch band sizes using the two input depth images of the wrist. For example, the two input depth images are a palm-facing depth map image and a side facing depth map image of the wrist. In some implementations, the ML model is trained on left and right arm data sets generated from live people, data sets generated from synthetic arm model databases including wrists (e.g., forearms, wrists, or hands), or combinations thereof. For example, a ground truth wrist circumference from a live subject may be provided by the data subject themselves or an assisting technician. In an example from a synthetic arm model database, a ground truth wrist circumference (e.g., cross-section) may be provided at a minimum circumference of the forearm or for a range along the longitudinal axis of the arm model. In some implementations, a convolutional neural network (CNN) is trained to regress on a wrist size based on the two views or a few (e.g., 5) views of the wrist, or a 3D mesh of the forearm within a preset distance of or range around (e.g., 10 cm) the styloid bone. In some implementations, the ML model may use RGB data (e.g., images captured during the scanning process) aligned with the depth map images. In some implementations, a segmentation mask identifying portions of the depth data corresponding to the wrist is input to the ML model, wherein the segmentation mask is generated based on a light-intensity sensor data (e.g., RGB data).

In various implementations, the ML model can be, but is not limited to being, a deep neural network (DNN), an encoder/decoder neural network, a convolutional neural network (CNN), or a generative adversarial neural network (GANN). In some implementations, the image data used to measure wrists is designated for automated processing (e.g., machine viewing and not human viewing) to address privacy concerns.

As described herein, the ML network may be trained using datasets that include possible obstructions such as shirt sleeves, accessories (e.g., rings, bracelets, etc.), or both. In some implementations, the ML network is trained to output a band size among a plurality of band sizes. Alternatively, the ML network is trained to output a wrist circumference, which is then mapped (e.g., automatically) to output the band size.

Figure 6:
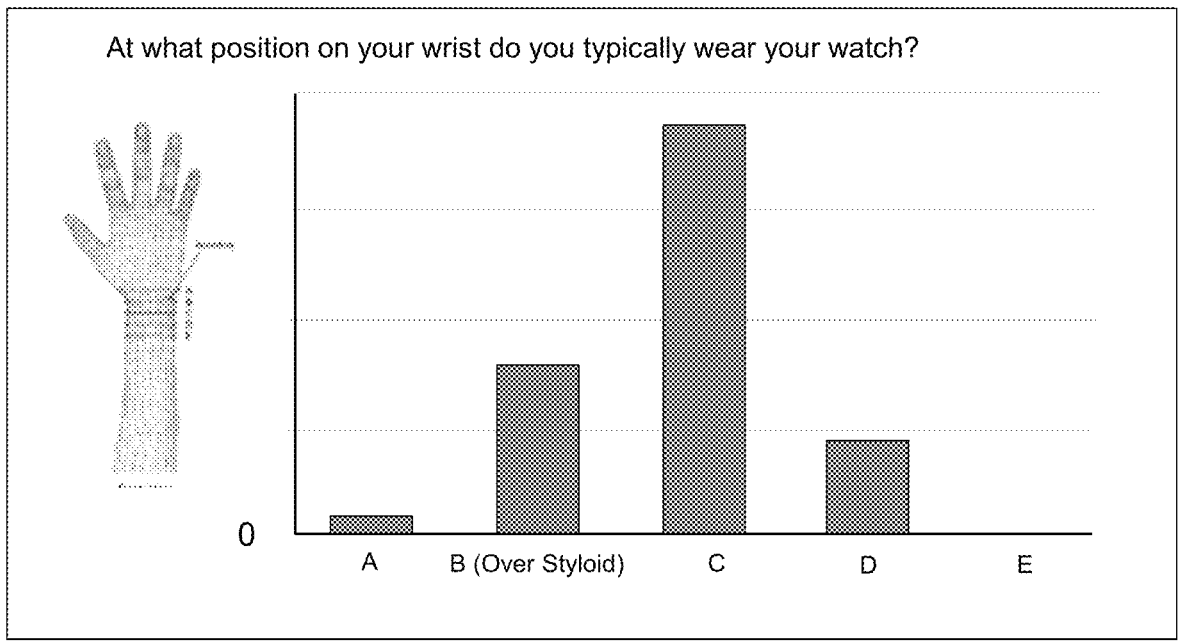
FIG. 6 illustrates an example of candidate locations along the forearm for a wrist measurement in accordance with some implementations.

In some implementations, a watch is worn in different places along the forearm (e.g., a plurality of watch/wrist locations). In some implementations, a wrist location is an input to the ML network and the ML network is further trained based on the user selecting one of a number (e.g., three, four, five) positions along the forearm for the wrist measurement (e.g., circumference). As shown in FIG. 6, a plurality of possible locations may be defined relative to the user's styloid bone. For example, position A is in front of the styloid bone, position B is over the styloid bone, position C is adjacent below the styloid bone, and position D and spaced away form and below the styloid bone. In another example a minimum circumference of the forearm is the wrist location (e.g., usually below the styloid bone).

Figure 7:
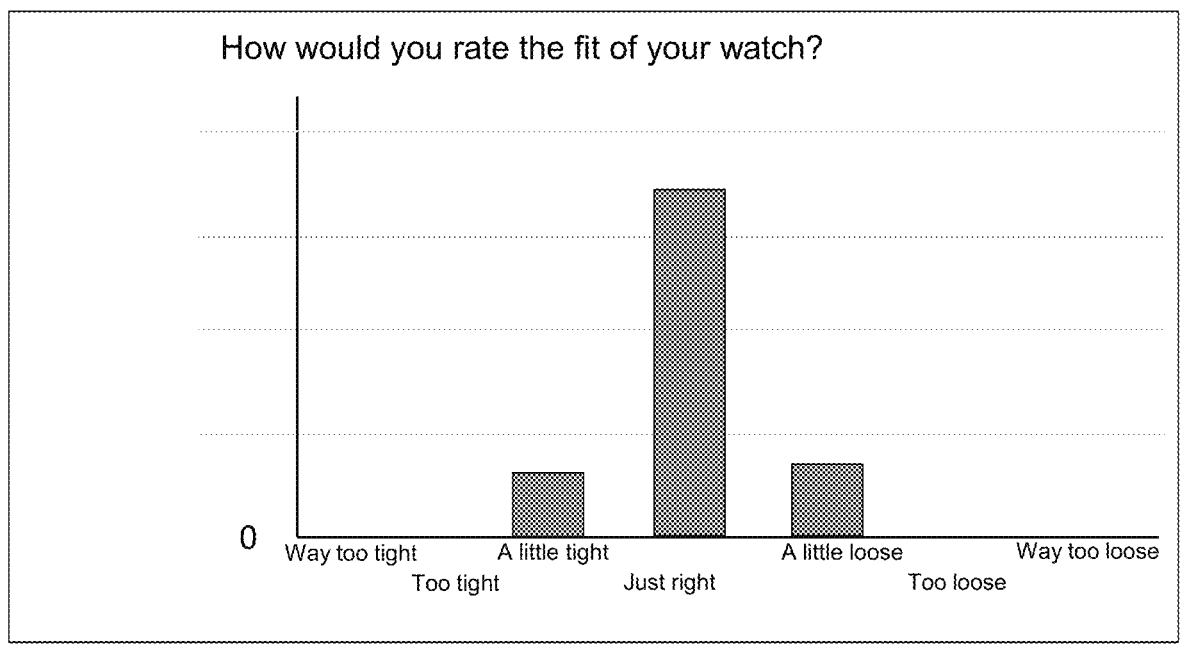
FIG. 7 illustrates an example of candidate tightness levels for a wrist measurement in accordance with some implementations.

In some implementations, a watch is worn with different levels of tightness (e.g., snugness) on the forearm (e.g., a plurality of tightness levels). In some implementations, a tightness level is an input to the ML network and the ML network is further trained based on the user selecting more than one tightness level for the wrist measurement (e.g., circumference). As shown in FIG. 7, a plurality of three tightness levels may be level A: tight and deforms the skin around the wrist, level B: snug and touches the skin around the wrist, or level C: loose and does not contact the skin along the entire circumference of the wrist. Alternatively, a tightness level could modify the wrist circumference by a preset distance such as 2 mm.

In some implementations, the wrist can be represented as an ellipsoid with 2 orthogonal variables (e.g., the width and length). However, the width and length measurements may change independent of each other, and accordingly, a single view of the wrist is insufficient to correctly determine a circumference of the wrist. Thus, at least two views of the wrist are needed, and the two views must be sufficiently apart in rotation to determine the circumference of the wrist (e.g., to control for both the independent width and length variables determining the ellipsoid). In some implementations, the rotation between the two different views of the wrist is at least 45°, 75°, or 90°.

In some implementations, additional views before the first depth measurement, between the first and second depth measurement, or after the second death measurement may be captured and used as input to the ML network.

In some implementations, the two depth images of the wrist included depth data for the fingers and hands or portions of the forearm up to the elbow. In one example, including the hand depth measurements (e.g., fist or fingers) in the two depth images of the wrist assisted with determining rotation and accurately modeling the ellipsoid representing the wrist. In another example, including the forearm measurements up to the elbow in the two depth images of the wrist did not appear to significantly improve the accuracy in the wrist measurement.

In some implementations, the ML network is adjusted to focus on the wrist portions of the two depth images. For example, input data within a preset distance from the styloid bone, or the minimum circumference of the forearm could be weighted to have greater influence in the ML network. In another example, input depth data from the hands or elbow area of the depth images could be weighted to have less influence in the ML network.

In some implementations, the depth images correspond to and are registered to images from an RGB image sensor. For example, each pixel in the RGB image has a corresponding depth value and the combined color and depth image (e.g., RGB-D) is the image used for each of the depth images.

In some implementations, the wrist measurement techniques provide a rest measurement that is accurate to within +/−1 mm, +/−3 mm, or +/−5 mm. In some implementations, the wrist measurement techniques reduce a number of purchased incorrectly sized watch bands that are subsequently returned or replaced. In one study, an average of at least seven millimeters (too large or too small) occurred in wrist measurements when a printable measurement tool or household items were used to measure the wrist.

In some implementations, the wrist measurement techniques described herein are implemented using a single wrist measurement (e.g., depth measurement, depth image, or depth data) of the wrist 110 captured by the depth sensor 122. In one example, the single wrist measurement of the wrist 110 may be captured with the palm facing down at the depth sensor 122 (e.g., see FIG. 2). In another example, the single wrist measurement of the wrist 110 may be captured with the palm facing angled 45°-90° above the depth sensor 122 (e.g., see FIG. 3). In one implementation, the single wrist measurement uses the combined color and depth image (e.g., RGB-D). In these implementations, the single depth measurement of the wrist is input into a corresponding ML model (e.g., as described herein) that was trained to output wrist measurements or 1 size from among the plurality of watch band sizes using the single depth measurement input (e.g., depth image of the wrist). In these implementations, an accuracy of the single wrist measurement was determined to be sufficient to identify a single watch band size (e.g., +/−5 mm), but less accurate than the implementations using the two depth measurements of the wrist from different angles. Further, guidance for positioning of the wrist 110 relative to the depth sensor 122 is significantly reduced (e.g., at least 50%). Accordingly, the single wrist measurement techniques may be implemented for a subset of users (e.g., blind users, young children) in a second operational mode (e.g., an accessible mode) because the single wrist measurement technique is easier to perform.

As shown in FIGS. 1-5, the user guidance to collect the two depth images of the wrist was visual guidance, However, the application is not intended to be so limited. In some examples the user guidance to collect the two depth measurements of the wrist is audible guidance. In some implementations, an audible guidance changes depending on a spatial distance (e.g., x/y and depth) from alignment. In one example, a frequency of beeping can change, (e.g., increase, decrease) as the wrist gets closer to alignment for one of the depth images, and then turn steady (e.g., continuous or no beeping) upon alignment. In another example, a pitch of an audible guidance signal changes as the wrist gets closer to alignment for one of the depth images. In some implementations, the audible guidance includes words and directions such as "move your wrist to the right slowly, . . . , now stop, . . . , you are aligned". In some implementations, the guidance is provided by haptic signals or feedback that create an experience of touch by applying forces, vibrations, or motions to direct the wrist into alignment for one of the depth images.

In some implementations, the depth sensor 122 is calibrated prior to the wrist measurement technique. For example, temperature fluctuations or physical collisions can impact the depth sensor and provide a bias to the depth measurements from the depth sensor 122. Accordingly, the depth sensor may be re-calibrated by holding a calibration target at a set distance and orientation to the depth sensor in a calibration process. Accordingly, in some implementations, the calibration target is specialized for the depth sensor 122 or is a common household object with a known size such as a credit card.

In some implementations, the depth sensor 122 is an active light stereo detection system. Alternatively, the depth sensor 122 is a plurality of depth sensors. In some implementations, the depth sensor 122 detects depth of the wrist based on known 2D or 3D object detection and localization algorithms, VIO information, infrared data, depth detection data, RGB-D data, other information, or some combination thereof.

Figure 8:
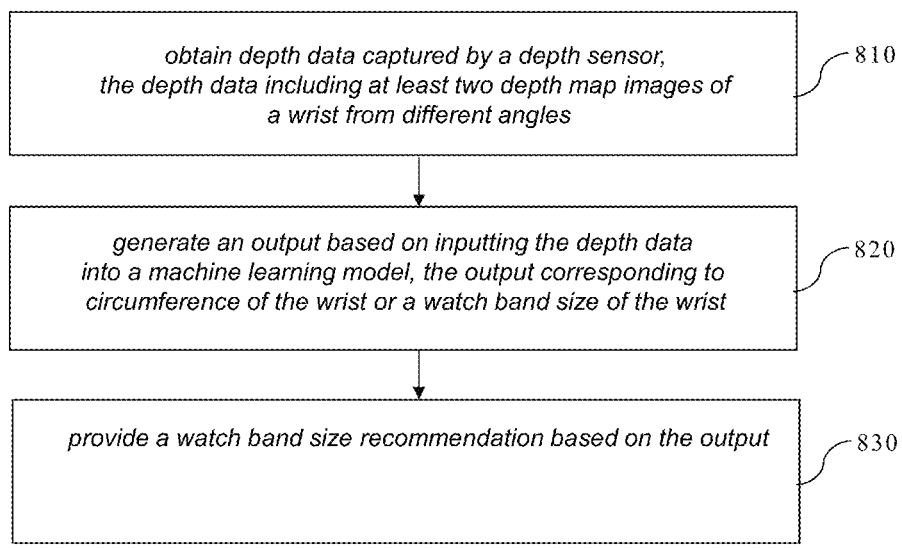
FIG. 8 is a flowchart illustrating an exemplary method of determining a wrist measurement or watch band size using depth data captured by a depth sensor in accordance with some implementations.

FIG. 8 is a flowchart illustrating an exemplary method of determining a wrist measurement or watch band size using depth data captured by a depth sensor. In some implementations, the depth data including at least two depth map images of a wrist are from different angles sufficient separated to accurately represent the wrist circumference. In some implementations, the measurement experience is touchless. In some implementations, the measurement experience is performed by an individual using an electronic device. In some implementations, the watch band is not adjustable, and an accurate wrist measurement is especially useful. In some implementations, the method 800 is performed by a device (e.g., electronic device 920, 1000 of FIGS. 9 and 10). The method 800 can be performed using an electronic device or by multiple devices in communication with one another. In some implementations, the method 800 is performed by processing logic, including hardware, firmware, software, or a combination thereof. In some implementations, the method 800 is performed by a processor executing code stored in a non-transitory computer-readable medium (e.g., a memory). In some implementations, the method 800 is performed by an electronic device having a processor.

At block 810, the method 800 obtains depth data captured by a depth sensor, the depth data including at least two depth map images of a wrist from different angles. In some implementations, the depth sensor is in a portable electronic device (e.g., a smartphone, a tablet, etc.). In some implementations, the electronic device is placed on a surface with the depth sensor facing up, and a user may rotate their hand/wrist above the electronic device during a wrist scanning process. In some implementations, the two depth map images are selected based on determining that the two depth map images correspond to at least a threshold difference in viewpoint (e.g., 90°) that is sufficient to capture two different ellipses used to represent the wrist circumference. For example, one of the depth map images of the user's wrist is captured with the palm facing the depth sensor and the other of the depth map images of the user's wrist is captured with the palm facing to the side. Optionally, the depth map images may include depth values for portions of a hand, all of the hand, and/or portions of the arm up to the elbow. In some implementations, guidance regarding positioning of the wrist or depth sensor is provided while the depth data is obtained.

The depth sensor may be one or more depth sensors (e.g., a structured light, a time-of-flight, or the like). Alternatively, the depth data may include a two-view depth pair of two depth map images. In some implementations, the depth data includes additional depth map images captured before, between, and after the two depth map images. In one implementation, two cameras and stereo imaging techniques (e.g., triangulation) may be used. In one implementation, a projector and an image sensor use structured light imaging techniques are used to determine the depth data.

At block 820, the method 800 generates an output based on inputting the depth data into a machine learning (ML) model, the output corresponding to circumference of the wrist or a watch band size of the wrist. In some implementations, the ML model is a convolutional neural network (CNN) regressor. In some implementations, the ML model may use RGB data aligned with the depth map images. In some implementations, a segmentation mask identifying portions of the depth data corresponding to the wrist is input to the ML model, wherein the segmentation mask is generated based on a light-intensity sensor data (e.g., RGB data). In some implementations, the ML model is trained using real ground truth data based on user measurements of real wrists and/or synthetic ground truth data that identifies a wrist circumference at a plurality of arm locations along the longitudinal axis of the forearm (e.g., near the styloid bone, or a minimal circumference along the forearm). Further, the ML model may be trained using training data that corresponds to watch tightness (e.g., does not touch the skin along a percentage of the circumference, touches wrist throughout circumference, or partially deforms the skin). In addition, the ML model may be trained based on weighted forearm measurements that may increase a relative significance of the measurements around the wrist (e.g., along a longitudinal axis of the forearm). In some implementations, the ML model also outputs a confidence value below which re-measurement of the wrist is recommended. Alternatively, the ML model outputs a confidence value corresponding to a confidence in the circumference of the wrist or the watch band size of the wrist.

At block 830, the method 800 provides a watch band size recommendation based on the output. In some implementations, the watch band size recommendation is a watch band size is selected among a plurality of watch band sizes (e.g., 5 sizes, 12 sizes, 15 sizes) or an actual wrist circumference measurement (e.g., 154 mm) that is mapped to a wrist band size. In one example, the watch band size recommendation is provided visually, in writing, audibly, or a combination thereof to the user.

In some implementations, the method 800 determines a wrist measurement or watch band size using a single depth measurement captured by a depth sensor. In these implementations, a single depth map image of a wrist is obtained at block 810, the single depth measurement is input into a ML model that generates an output corresponding to a circumference of the wrist or a watch band size of the wrist at block 820, and a watch band size recommendation is provided based on the output at block 830. In one implementation at block 810, the single wrist measurement is captured with the palm facing a depth sensor (e.g., see FIG. 2) that captures a combined color and depth data (e.g., RGB-D) as the single depth measurement.

In some implementations, the electronic device is a portable electronic device such as a smartphone or a tablet. In some implementations, the electronic device is an HMD. For example, techniques disclosed herein may be implemented on an HMD that provides an optical-see through view or a video pass-through view of a surrounding physical environment.

Figure 9:
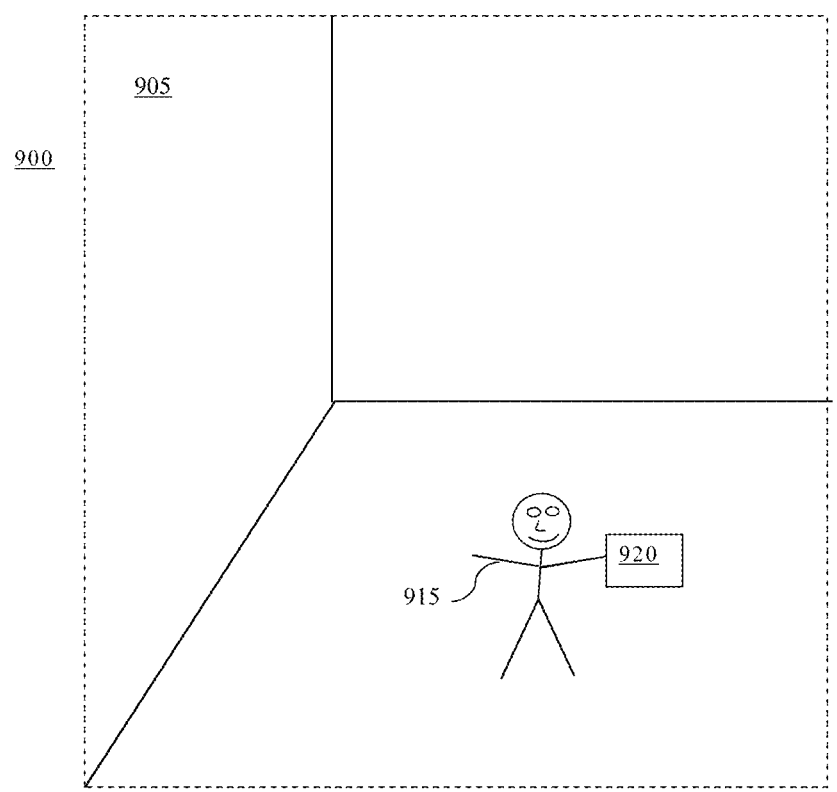
FIG. 9 illustrates an example operating environment in accordance with some implementations.

FIG. 9 illustrates an example operating environment 900 in which electronic device 920 is used in physical environment 905. A physical environment refers to a physical world that people can interact with and/or sense without the aid of electronic systems. A physical environment refers to a physical world that people can sense and/or interact with without aid of electronic devices. The physical environment may include physical features such as a physical surface or a physical object. For example, the physical environment corresponds to a physical park that includes physical trees, physical buildings, and physical people. People can directly sense and/or interact with the physical environment such as through sight, touch, hearing, taste, and smell. In contrast, an extended reality (XR) environment refers to a wholly or partially simulated environment that people sense and/or interact with via an electronic device. For example, the XR environment may include augmented reality (AR) content, mixed reality (MR) content, virtual reality (VR) content, and/or the like. With an XR system, a subset of a person's physical motions, or representations thereof, are tracked, and, in response, one or more characteristics of one or more virtual objects simulated in the XR environment are adjusted in a manner that comports with at least one law of physics. As one example, the XR system may detect head movement and, in response, adjust graphical content and an acoustic field presented to the person in a manner similar to how such views and sounds would change in a physical environment. As another example, the XR system may detect movement of the electronic device presenting the XR environment (e.g., a mobile phone, a tablet, a laptop, or the like) and, in response, adjust graphical content and an acoustic field presented to the person in a manner similar to how such views and sounds would change in a physical environment. In some situations (e.g., for accessibility reasons), the XR system may adjust characteristic(s) of graphical content in the XR environment in response to representations of physical motions (e.g., vocal commands).

There are many different types of electronic systems that enable a person to sense and/or interact with various XR environments. Examples include head mountable systems, projection-based systems, heads-up displays (HUDs), vehicle windshields having integrated display capability, windows having integrated display capability, displays formed as lenses designed to be placed on a person's eyes (e.g., similar to contact lenses), headphones/earphones, speaker arrays, input systems (e.g., wearable or handheld controllers with or without haptic feedback), smartphones, tablets, and desktop/laptop computers. A head mountable system may have one or more speaker(s) and an integrated opaque display. Alternatively, a head mountable system may be configured to accept an external opaque display (e.g., a smartphone). The head mountable system may incorporate one or more imaging sensors to capture images or video of the physical environment, and/or one or more microphones to capture audio of the physical environment. Rather than an opaque display, a head mountable system may have a transparent or translucent display. The transparent or translucent display may have a medium through which light representative of images is directed to a person's eyes. The display may utilize digital light projection, OLEDs, LEDs, uLEDs, liquid crystal on silicon, laser scanning light source, or any combination of these technologies. The medium may be an optical waveguide, a hologram medium, an optical combiner, an optical reflector, or any combination thereof. In some implementations, the transparent or translucent display may be configured to become opaque selectively. Projection-based systems may employ retinal projection technology that projects graphical images onto a person's retina. Projection systems also may be configured to project virtual objects into the physical environment, for example, as a hologram or on a physical surface.

In the example of FIG. 9, the device 920 is illustrated as a single device. Some implementations of the device 920 are hand-held. For example, the device 920 may be a mobile phone, a tablet, a laptop, and so forth. In some implementations, the device 920 is worn by a user 915. For example, the device 920 may be a watch, a head-mounted device (HMD), and so forth. In some implementations, functions of the device 920 are accomplished via two or more devices, for example additionally including an optional base station. Other examples include a laptop, desktop, server, or other such device that includes additional capabilities in terms of power, CPU capabilities, GPU capabilities, storage capabilities, memory capabilities, and the like. The multiple devices that may be used to accomplish the functions of the device 920 may communicate with one another via wired or wireless communications.

Figure 10:
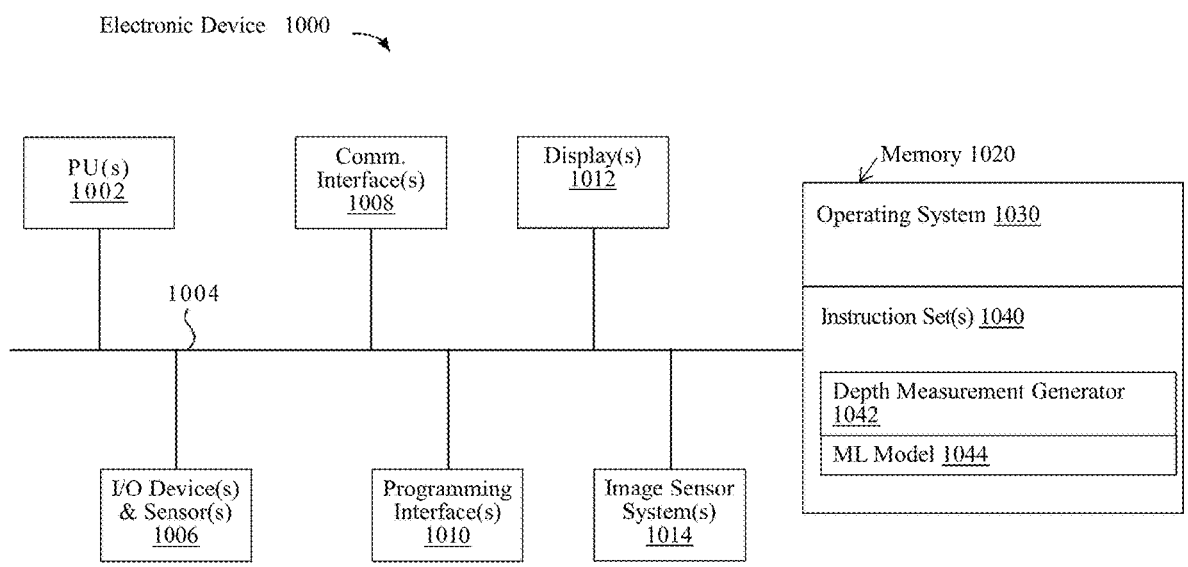
FIG. 10 illustrates an example electronic device in accordance with some implementations.

FIG. 10 is a block diagram of an example device 1000. Device 1000 illustrates an exemplary device configuration for the device 920. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the electronic device 1000 includes one or more processing units 1002 (e.g., microprocessors, ASICs, FPGAs, GPUs, CPUs, processing cores, or the like), one or more input/output (I/O) devices and sensors 1006, one or more communication interfaces 1008 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, SPI, I2C, or the like type interface), one or more programming (e.g., I/O) interfaces 1010, one or more displays 1012, one or more interior or exterior facing sensor systems 1014, a memory 1020, and one or more communication buses 1004 for interconnecting these and various other components.

In some implementations, the one or more communication buses 1004 include circuitry that interconnects and controls communications between system components. In some implementations, the one or more I/O devices and sensors 1006 include at least one of an inertial measurement unit (IMU), an accelerometer, a magnetometer, a gyroscope, a thermometer, one or more physiological sensors (e.g., blood pressure monitor, heart rate monitor, blood oxygen sensor, blood glucose sensor, etc.), one or more microphones, one or more speakers, a haptics engine, one or more depth sensors (e.g., a structured light, a time-of-flight, or the like), or the like.

In some implementations, the one or more displays 1012 are configured to present content to the user. In some implementations, the one or more displays 1012 correspond to holographic, digital light processing (DLP), liquid-crystal display (LCD), liquid-crystal on silicon (LCoS), organic light-emitting field-effect transitory (OLET), organic light-emitting diode (OLED), surface-conduction electron-emitter display (SED), field-emission display (FED), quantum-dot light-emitting diode (QD-LED), micro-electro-mechanical system (MEMS), or the like display types. In some implementations, the one or more displays 1012 correspond to diffractive, reflective, polarized, holographic, etc. waveguide displays. For example, the electronic device 1000 may include a single display. In another example, the electronic device 1000 includes a display for each eye of the user.

In some implementations, the one or more interior or exterior facing sensor systems 1014 include an image capture device or array that captures image data or an audio capture device or array (e.g., microphone) that captures audio data. The one or more image sensor systems 1014 may include one or more RGB cameras (e.g., with a complimentary metal-oxide-semiconductor (CMOS) image sensor or a charge-coupled device (CCD) image sensor), monochrome cameras, IR cameras, or the like. In various implementations, the one or more image sensor systems 1014 further include an illumination source that emits light such as a flash. In some implementations, the one or more image sensor systems 1014 further include an on-camera image signal processor (ISP) configured to execute a plurality of processing operations on the image data.

The memory 1020 includes high-speed random-access memory, such as DRAM, SRAM, DDR RAM, or other random-access solid-state memory devices. In some implementations, the memory 1020 includes non-volatile memory, such as one or more magnetic disk storage devices, optical disk storage devices, flash memory devices, or other non-volatile solid-state storage devices. The memory 1020 optionally includes one or more storage devices remotely located from the one or more processing units 1002. The memory 1020 comprises a non-transitory computer readable storage medium.

In some implementations, the memory 1020 or the non-transitory computer readable storage medium of the memory 1020 stores an optional operating system 1030 and one or more instruction set(s) 1040. The operating system 1030 includes procedures for handling various basic system services and for performing hardware dependent tasks. In some implementations, the instruction set(s) 1040 include executable software defined by binary information stored in the form of electrical charge. In some implementations, the instruction set(s) 1040 are software that is executable by the one or more processing units 1002 to carry out one or more of the techniques described herein.

In some implementations, the instruction set(s) 1040 include a depth measurement generator 1042 that is executable by the processing unit(s) 1002 to capture at least two depth measurements of a wrist from different angles sufficient to accurately represent the wrist circumference according to one or more of the techniques disclosed herein. In some implementations, the instruction set(s) 1040 include a ML model 1044 that is executable by the processing unit(s) 1002 to output a wrist measurement based on the at least two depth measurements of a wrist according to one or more of the techniques disclosed herein.

Although the instruction set(s) 1040 are shown as residing on a single device, it should be understood that in other implementations, any combination of the elements may be located in separate computing devices. FIG. 10 is intended more as a functional description of the various features which are present in a particular implementation as opposed to a structural schematic of the implementations described herein. As recognized by those of ordinary skill in the art, items shown separately could be combined and some items could be separated. For example, actual number of instruction sets and the division of particular functions and how features are allocated among them will vary from one implementation to another and, in some implementations, depends in part on the particular combination of hardware, software, or firmware chosen for a particular implementation.

It will be appreciated that the implementations described above are cited by way of example, and that the present invention is not limited to what has been particularly shown and described hereinabove. Rather, the scope includes both combinations and sub combinations of the various features described hereinabove, as well as variations and modifications thereof which would occur to persons skilled in the art upon reading the foregoing description and which are not disclosed in the prior art.

Those of ordinary skill in the art will appreciate that well-known systems, methods, components, devices, and circuits have not been described in exhaustive detail so as not to obscure more pertinent aspects of the example implementations described herein. Moreover, other effective aspects and/or variants do not include all of the specific details described herein. Thus, several details are described in order to provide a thorough understanding of the example aspects as shown in the drawings. Moreover, the drawings merely show some example embodiments of the present disclosure and are therefore not to be considered limiting.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Alternatively, or additionally, the program instructions can be encoded on an artificially generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures. Unless specifically stated otherwise, it is appreciated that throughout this specification discussions utilizing the terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general purpose computing apparatus to a specialized computing apparatus implementing one or more implementations of the present subject matter. Any suitable programming, scripting, or other type of language or combinations of languages may be used to implement the teachings contained herein in software to be used in programming or configuring a computing device.

Implementations of the methods disclosed herein may be performed in the operation of such computing devices. The order of the blocks presented in the examples above can be varied for example, blocks can be re-ordered, combined, and/or broken into sub-blocks. Certain blocks or processes can be performed in parallel. The operations described in this specification can be implemented as operations performed by a data processing apparatus on data stored on one or more computer-readable storage devices or received from other sources.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or value beyond those recited. Headings, lists, and numbering included herein are for ease of explanation only and are not meant to be limiting.

It will also be understood that, although the terms "first," "second," etc. may be used herein to describe various elements, these elements should not be limited by these terms. These terms are only used to distinguish one element from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

What is claimed is:

1. A method comprising:
at an electronic device having a processor:
obtaining depth data captured by a depth sensor, the depth data comprising a set of depth map images of a wrist from different angles, wherein the set of depth map images are captured with different portions of the wrist facing the depth sensor;
selecting at least two depth map images from the set based on determining that the two depth map images correspond to at least a minimum threshold difference in viewpoint with respect to an angle of the different angles;
generating an output based on inputting the depth data into a machine learning model, the output corresponding to circumference of the wrist or a watch band size of the wrist; and
providing a watch band size recommendation based on the output.

2. The method of claim 1, wherein the machine learning model is a convolutional neural network regressor.

3. The method of claim 1, wherein a segmentation mask identifying portions of the depth data corresponding to the wrist is input to the machine learning model, wherein the segmentation mask is generated based on a light-intensity sensor data.

4. The method of claim 1, wherein the machine learning model is trained using real and synthetic training data.

5. The method of claim 1, wherein the machine learning model is trained using training data that identifies a wrist circumference at a plurality of arm locations.

6. The method of claim 1, wherein the machine learning model is trained using training data that corresponds to watch tightness.

7. The method of claim 1, wherein the machine learning model is trained based on weighted forearm measurements, wherein weights of the weighted forearm measurements correspond to relative significance of the weighted forearm measurements along an axis of an arm.

8. The method of claim 1, wherein the machine learning model further outputs a confidence value corresponding to a confidence in the circumference of the wrist or the watch band size of the wrist.

9. The method of claim 1, wherein the depth data comprises a two-view depth pair of two depth map images.

10. The method of claim 9, wherein the depth data comprises additional depth map images before, between, and after the two depth map images.

11. The method of claim 1, wherein the at least two depth map images are captured as the wrist is rotated in front of the depth sensor.

12. The method of claim 1, wherein guidance regarding positioning of the wrist or depth sensor is provided while the depth data is obtained.

13. The method of claim 1, wherein the at least two depth map images each comprise depth values for portions of a hand.

14. The method of claim 1, wherein the electronic device is a mobile phone or tablet.

15. The method of claim 1, wherein the watch band size recommendation is associated with a non-adjustable watch band.

16. The method of claim 1, wherein the at least a minimum threshold difference in viewpoint is selected based on identifying at least two different ellipse parameters representing shape and size of the wrist to determine the circumference of the wrist.

17. The method of claim 1, wherein the at least two depth map images further comprise portions of an arm located above the wrist.

18. A system comprising:
memory; and
one or more processors at a device coupled to the memory, wherein the memory comprises program instructions that, when executed on the one or more processors, cause the system to perform operations comprising:
obtaining depth data captured by a depth sensor, the depth data comprising a set of depth map images of a wrist from different angles, wherein the set of depth map images are captured with different portions of the wrist facing the depth sensor;
selecting at least two depth map images from the set based on determining that the two depth map images correspond to at least a minimum threshold difference in viewpoint with respect to an angle of the different angles;
generating an output based on inputting the depth data into a machine learning model, the output corresponding to circumference of the wrist or a watch band size of the wrist; and
providing a watch band size recommendation based on the output.

19. The system of claim 18, wherein the at least two depth map images are selected based on determining that the at least two depth map images correspond to at least a threshold difference in rotation of the wrist around a longitudinal axis of an arm.

20. A non-transitory computer-readable storage medium, storing program instructions executable via one or more processors to perform operations comprising:
obtaining depth data captured by a depth sensor, the depth data comprising a set of depth map images of a wrist from different angles, wherein the set of depth map images are captured with different portions of the wrist facing the depth sensor;
selecting at least two depth map images from the set based on determining that the two depth map images correspond to at least a minimum threshold difference in viewpoint with respect to an angle of the different angles;
generating an output based on inputting the depth data into a machine learning model, the output corresponding to circumference of the wrist or a watch band size of the wrist; and
providing a watch band size recommendation based on the output.

* * * * *